(12) United States Patent
Beaulieu

(10) Patent No.: US 7,956,624 B2
(45) Date of Patent: Jun. 7, 2011

(54) METHOD AND SYSTEM FOR MONITORING GROWTH CHARACTERISTICS

(76) Inventor: Kelly Beaulieu, Portage la Prairie (CA)

( * ) Notice: Subject to any disclaimer, the term of this patent is extended or adjusted under 35 U.S.C. 154(b) by 254 days.

(21) Appl. No.: 12/300,035

(22) PCT Filed: May 7, 2007

(86) PCT No.: PCT/CA2007/000797
§ 371 (c)(1),
(2), (4) Date: Apr. 20, 2009

(87) PCT Pub. No.: WO2007/128122
PCT Pub. Date: Nov. 15, 2007

(65) Prior Publication Data
US 2009/0322357 A1    Dec. 31, 2009

Related U.S. Application Data

(60) Provisional application No. 60/798,321, filed on May 8, 2006.

(51) Int. Cl.
*G01R 27/08* (2006.01)
(52) U.S. Cl. ........... 324/692; 324/716
(58) Field of Classification Search ........... 324/692, 324/716; 73/73
See application file for complete search history.

(56) References Cited

U.S. PATENT DOCUMENTS

| | | | |
|---|---|---|---|
| 3,944,916 A | | 3/1976 | Tillander |
| 3,967,198 A | * | 6/1976 | Gensler ........... 324/72 |
| 4,069,716 A | * | 1/1978 | Vanasco et al. ........... 73/432.1 |
| 4,432,233 A | | 2/1984 | Tollner |
| 6,870,376 B1 | * | 3/2005 | Gensler ........... 324/664 |

* cited by examiner

*Primary Examiner* — Vincent Q Nguyen
(74) *Attorney, Agent, or Firm* — Ade & Company Inc.; Ryan W. Dupuis; Kyle R. Satterthwaite

(57) ABSTRACT

A system monitors growth characteristics of a plant having a root buried in a prescribed volume of ground using a plurality of electrodes inserted into the ground at a known spacing relative to one another in proximity to the root or root-like structure. When electrical current is applied to some of the electrodes, electrical potential is measured at other ones of the electrodes to construct a representation of electrical impedance across the prescribed volume locating the root or root-like structure. Growth characteristics of the soil and the plant, for example root size, root shape, soil moisture content, and the like, can be identified by locating variations of the electrical impedance.

20 Claims, 3 Drawing Sheets

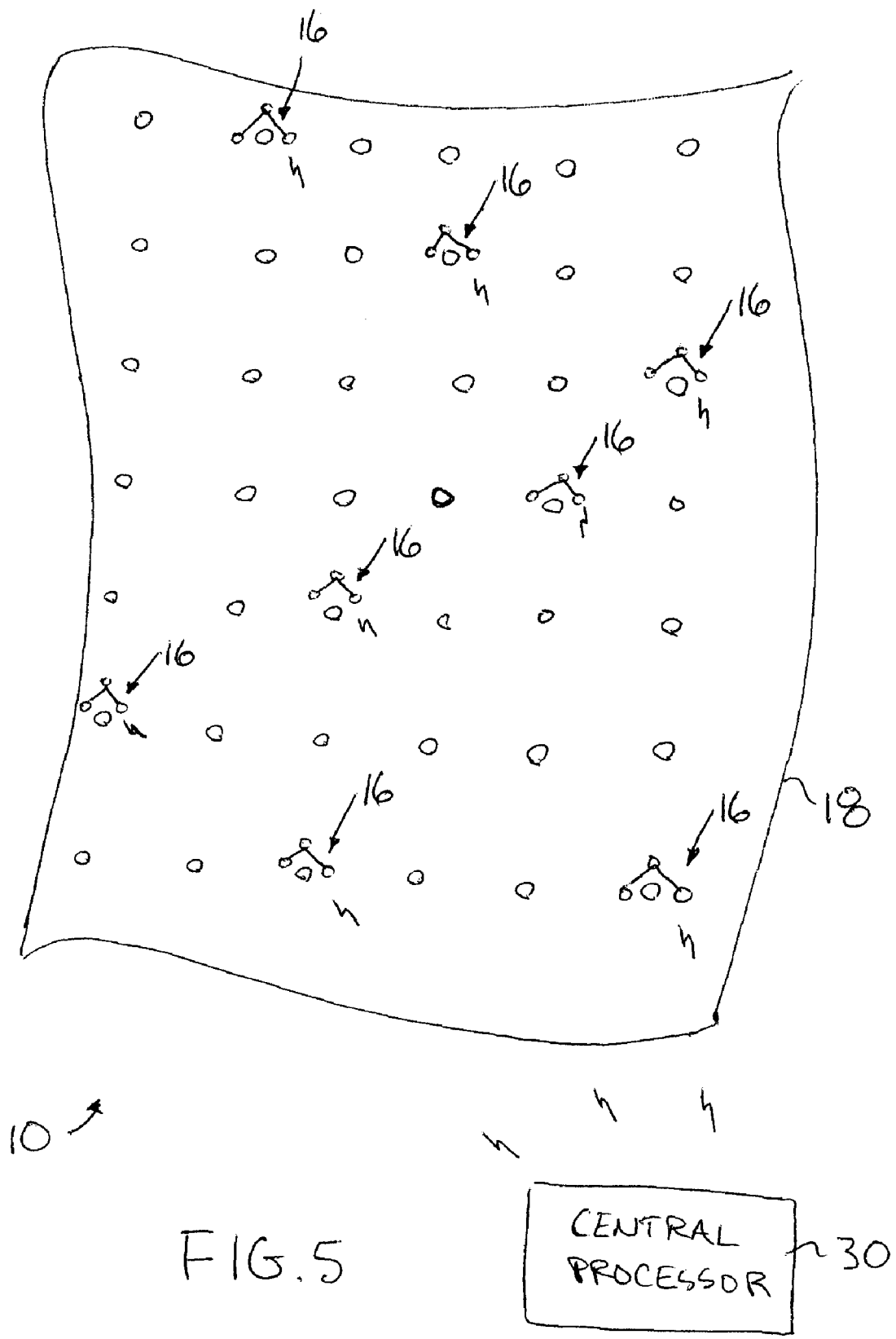

METHOD AND SYSTEM FOR MONITORING GROWTH CHARACTERISTICS

This application is a national phase filing of PCT/CA2007/000797 and claims the benefit under 35 U.S.C. 119(e) of U.S. provisional application Ser. No. 60/798,321, filed May 8, 2006.

FIELD OF THE INVENTION

The present invention relates to a method and a system which make use of electrical impedance for assessing various growth characteristics related to plants and crops, for example soil moisture content, soil fertility patterns, or tuber and/or root characteristics including size or shape, etc.

BACKGROUND

When growing root crops, for example potatoes, carrots and the like, it is difficult to monitor various growth characteristics of the crop because the root or associated root-like structures are buried in the ground. Sampling of the progress of the growth of the root or root-like structure thus requires destructive sampling by unearthing the root or root-like structures. Due to this inconvenience, less sampling is done, resulting in such conditions as disease or underdevelopment due to lack of water or fertilizer going undetected. At the same time, to optimize growing conditions it is desirable to monitor other growth characteristics in addition to the size and mass of the roots or roots-like structures, including soil moisture content and the like.

Electrical Impedance Tomography (EIT) is a known technology developed to image the electrical conductivity distribution of a conductive medium. The technology is of interest because of its low cost and also because the measurement of electrical conductivity brings direct information about the composition of the conductive medium. Until recently EIT has been researched primarily for medical application. The technology has also been applied in the soil for the purpose of detecting landmines and unexploded ordinances. The detection process essentially measures three-dimensional perturbations in the local environmental electrical conductivity.

SUMMARY OF THE INVENTION

According to one aspect of the invention there is provided a method of monitoring growth characteristics of a plant having a root or root-like structure buried in a prescribed volume of ground, the method comprising:

locating a plurality of electrodes at a known spacing relative to one another in the prescribed volume in proximity to the root or root-like structure;

applying an electrical current to some of the electrodes;

measuring electrical potential at some of the electrodes while the electrical current is applied;

constructing a representation of electrical impedance across the prescribed volume using the measured electrical potential and the known spacing of the electrodes; and identifying a growth characteristic in the prescribed volume by locating variations of electrical impedance in the representation of electrical impedance across the prescribed volume.

When the variations of electrical impedance comprise a region or volume, the method preferably includes identifying size of a root or root-like structure as defined by the variation of electrical impedance.

When the variation of electrical impedance comprises a boundary or contour between two regions of differing electrical impedance, the method preferably includes identifying shape of a root or root-like structure as defined by the variation of electrical impedance.

The method may include identifying variations of electrical impedance over time intervals to determine variations in moisture content in the ground.

A given moisture level of the soil may be determined by comparing the electrical impedance in the representation of electrical impedance across the prescribed volume of ground to a calibrated base level electrical impedance.

The electrodes are preferably inserted into the ground spaced below a surface of the ground.

A representation of electrical impedance across the prescribed volume of ground at spaced intervals of time may be constructed and a growth characteristic be identified by comparing the representation of electrical impedance at different ones of the intervals of time.

The temperature in the ground is preferably measured in proximity to the electrodes and taken into consideration.

A representation of electrical impedance across the prescribed volume of ground may be constructed in association with one plant and then repeated for a plurality of plants across a given region.

Characteristics of the ground may also be assessed by comparing a constructed representation of electrical impedance of one region with another region.

The representations of electrical impedance across the prescribed volume of ground may be associated with an existing field map generated by field mapping software.

The electrodes may be supported on a portable probe including a portable processor coupled therewith which is arranged to construct the representation of electrical impedance across the prescribed volume of ground.

A representation of electrical impedance for a plurality of plants within a given region may be constructed by providing a sensor including electrodes thereon associated with each plant.

Preferably each sensor includes GPS location data and a unique ID associated therewith. Each sensor may also include data storage means and a transmitter for communicating data to a central processor. The transmitter preferably only transmits data responsive to receipt of a password.

The electrodes are preferably calibrated for a prescribed root type or root-like structure by varying the relative positioning and spacing between the electrodes.

According to a second aspect of the present invention there is provided a crop monitoring system for monitoring a growth characteristic of a plant having a root or root-like structure buried in a prescribed volume of ground, the system comprising:

a plurality of electrodes inserted into the prescribed volume of ground in proximity to the root or root-like structure and at a known spacing relative to one another;

current means arranged apply a current to at least some of the electrodes;

measuring means arranged to measure an electrical potential of at least some of the electrodes during a current being applied;

processor means arranged to receive the electrical potentials from the measuring means, to construct a representation of electrical impedance across the prescribed volume, and to identify variations of electrical impedance in the representation of electrical impedance across the prescribed volume.

The processor means may be arranged to identify size or shape of a root by locating variations of electrical impedance in the representation across the prescribed volume of ground.

The processor means may further be arranged to identify an overall electrical impedance of the ground and determine a difference between the overall electrical impedance and a calibrated base level impedance to determine a moisture level of the soil in the ground.

It has been discovered that electrical impedance tomography (EIT) can be adapted for constructing a representation of the root or root-like structures of a crop by inserting appropriate electrodes into the ground in proximity to the root or root-like structure to allow for efficient non-destructive testing to be done. Accordingly various problem conditions including disease or lack of water and the like can be detected at an early date for minimizing damage to the crop.

Two root crop monitoring (RCM) systems are disclosed herein as follows:

1. Seasonally installed stationary monitors in a system of control plots positioned throughout the field in a typical survey pattern—each of the stationary sensor units would independently log data and transmit that data to a central location at defined intervals.

The sensor system consists of a triad of stakes, though this configuration may vary for different crops. Each stake is approximately 24 inches in length and is studded with electrodes and sensors. This will image the tubers in three dimensions and also provide soil moisture readings. The data recording and download intervals can be set by the operator.

A placement template will accompany the device to ensure that placement of the stakes is always consistent. The template is set down, the stakes inserted and then the template is removed and used to place the next set of stakes. The stakes are robust enough to be utilized over many field seasons. In some cases the stakes may also be joined together permanently as a means of keeping the stakes correctly positioned.

2. The second root crop monitoring system consists of a portable monitoring device that can be used to diagnose suspected problem zones in the field (based on information received from the stationary units or visual identification) and can be used to survey fields that are not equipped with the stationary monitoring system. This portable device can also act as the data processing unit and will be capable of communicating directly to either a home-based computer system or to a centralized network.

The root crop monitor provides precise information to the grower about the size, shape and distribution of the root or root-like structure or tubers in the ground by passing an electrical current through the soil medium and differentiating the interface between the root or root-like structure or tuber and the surrounding soil. The detection process essentially measures three-dimensional perturbations in the local environmental electrical conductivity. The electrical current source and the data sensors are mounted inside the 24 inch long stakes. The stimulator electrodes will fire a small electrical pulse into the soil and the data recorder electrodes will act as sensors that detect the perturbations in the electrical field caused by the presence of the root or root-like structure or tuber tissue. A computer system with novel algorithms identifies conductivity perturbations within the volume. The sensor array has a volume capacity of approximately 24 inches×24 inches×24 inches, basically a cube 24 inches square.

Some embodiments of the invention will now be described in conjunction with the accompanying drawings in which:

BRIEF DESCRIPTION OF THE DRAWINGS

FIG. 5 is a schematic plan view of the sensor placement in the crop monitoring system according to the second embodiment.

In the drawings like characters of reference indicate corresponding parts in the different figures.

DETAILED DESCRIPTION

Figure 1:
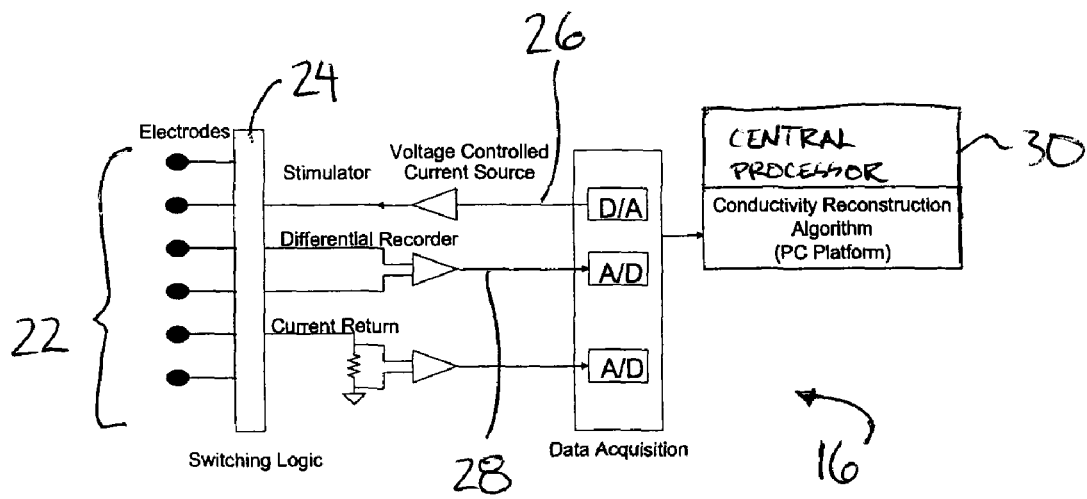
FIG. 1 is a schematic view of a sensor of the crop monitoring system according to the present invention.

Referring to the accompanying figures there is illustrated a crop monitoring system generally indicated by reference numeral 10. The system 10 is particularly suited for monitoring growth characteristics of a plant having a root or root-like structure 12 which is buried in prescribed volume of ground 14. As described herein, a root or root-like structure is understood to comprise the buried portion of a plant or crop including the root mass, tubers, various underground fibrous tissues and the like.

More particularly, roots are generally understood to be the underground portion of a plant that typically lacks buds, leaves or nodes and serves as support for the plant. The roots draw minerals and water from surrounding soil and can also act as food storage systems for the plant. Furthermore, root-like structures are generally understood to be modified underground stems usually fleshy modified leaves or stem tissues that contain stored food, for example: bulbs, corms, rhizomes, or tubers.

Although two embodiments are shown in the accompanying figures, the common features of each will first be described herein.

The system 10 includes one or more sensor portions 16 in which each sensor portion is associated with one respective plant within a crop in a given region 18. Each sensor 16 includes a set of three stakes 20 supporting a plurality of electrodes 22 at a known spacing therealong. Spacing between the electrodes can be varied when calibrating the sensor for different types of crops.

The stakes are inserted into the ground in a triangular pattern when viewed from above to at least partially surround the plant with which the sensor 16 is associated. Each sensor includes a switching logic component 24 which selectively couples the electrodes to either a current source 26 or a differential recorder 28. The switching logic is arranged so that during a measurement some of the electrodes have an electrical current applied thereto while some of the other electrodes can be used to measure electrical potential at a given location by the differential recorder 28.

Suitable digital analog converters acquire the data for communication to a processor 30 which makes use of the measured electrical potentials and the known spacing between the electrodes and between the stakes supporting the electrodes thereon to reconstruct a representation of electrical impedance across the prescribed volume of ground within which the plant root or root-like structures are buried. Variations of electrical impedance in the representation across the prescribed volume of ground can thus be used to identify various growth characteristics associated with the root or root-like structures. Firstly a boundary between the regions of differing electrical impedance can identify to the user the shape of a root or root-like structure by identifying the boundary or contour thereof. The overall volume or region of differing electrical impedance can also determine the size of the root or root-like structure buried in the ground.

Alternatively, the processor can compare the electrical impedance across the volume of ground over different intervals of time to identify an overall variation of the electrical impedance of the ground which may indicate a change in moisture. By first recording a base level profile of electrical impedance across the ground, the moisture level of the soil can thus be determined at a later date by comparison of the electrical impedance profile at any given time to the base level profile. The differences between the electrical impedance profiles can thus be correlated to a difference in moisture content assuming other characteristics remain constant.

A profile of varying moisture along either a linear path, a planar area or a throughout a volume can be generated by the present invention, as opposed to single point measurement probes of the prior art, due to the plurality of electrodes which can be spaced both vertically along the stakes and horizontally on different stakes. The electrodes of each stake are also cycled between which ones provide current and which ones record electrical potential during a measurement cycle to increase the number of measurements that can be taken by each set of electrodes.

Other conditions which may vary include temperature, pH level etc. In order to calibrate the electrodes for various temperature conditions, a temperature probe is provided on each of the stakes of each sensor 16 for measurement whenever electrical impedance is measured to ensure accuracy in the constructed representation of electrical impedance across the prescribed volume.

Figure 2:
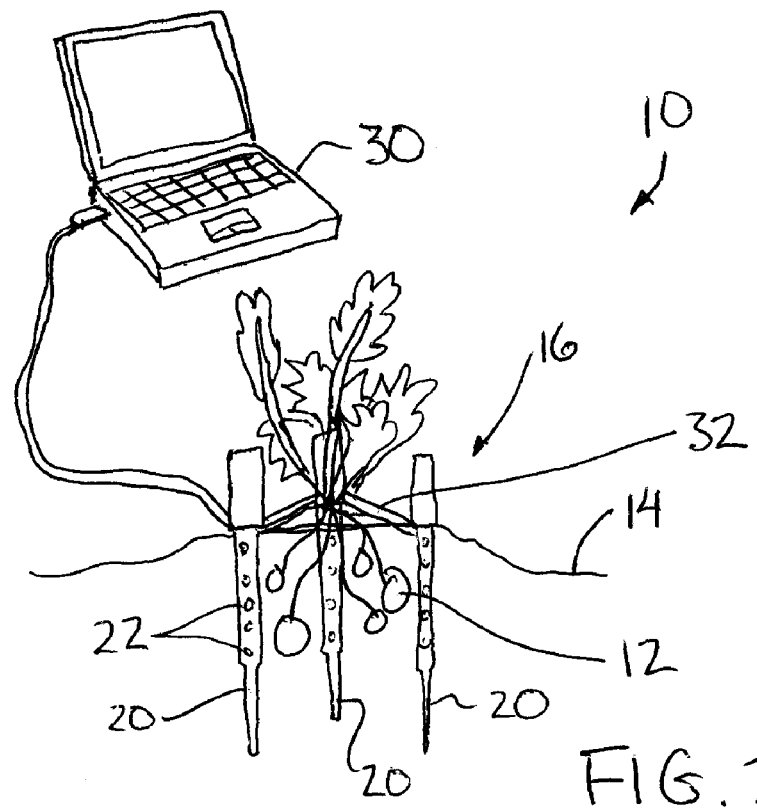
FIG. 2 is a perspective view of a first embodiment of the sensor.

Turning now more particularly to the embodiment of FIG. 2, the first embodiment of the system includes sensors 16 which are portable and which communicate with a central processor 30 in direct proximity therewith. The three stakes forming the sensor 16 in this instance are maintained at fixed spacing by suitable spacer bars 32 rigidly coupled between the stakes for controlling the relative positioning therebetween. The processor in this instance comprises a laptop which receives the data from all three stakes of the sensor. The processor in this instance also includes GPS equipment for associating global positioning satellite data with each measurement being taken. Accordingly a field map can be generated when moving the stakes from one plant to another across the prescribed region 18 being sampled.

Figure 3:
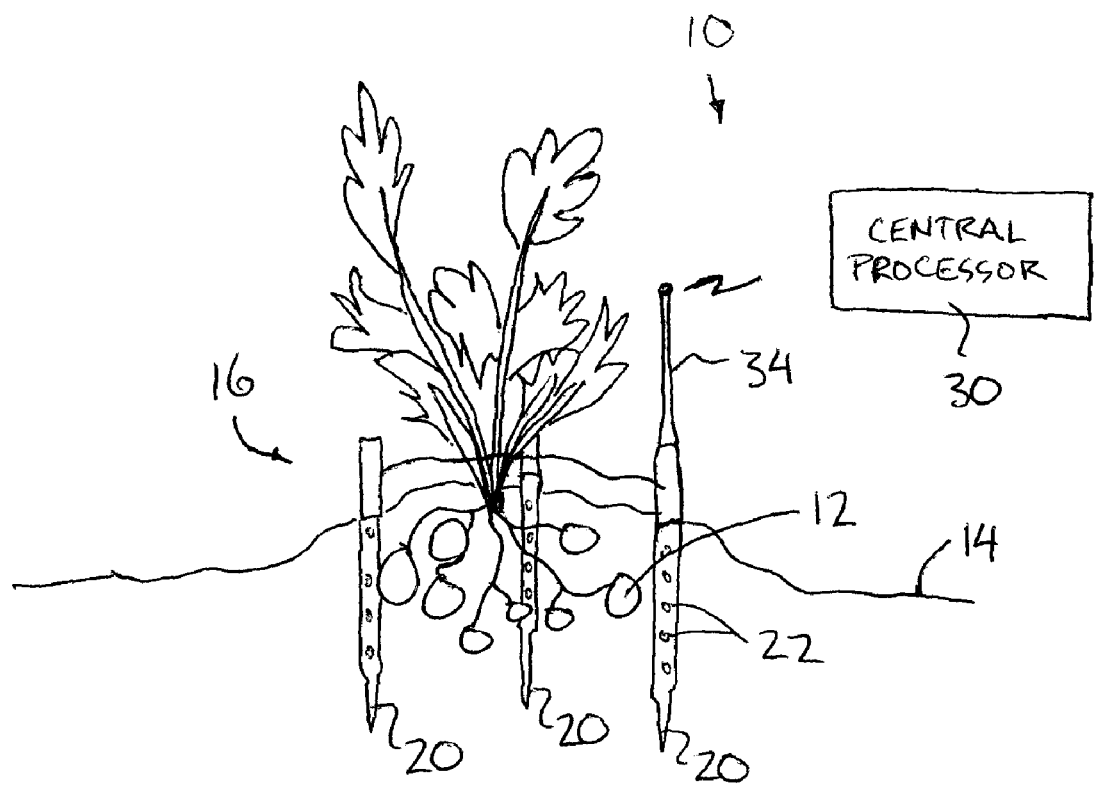
FIG. 3 is a side elevational view of a second embodiment of the sensor.
Figure 4:
FIG. 4 is a top plan view of a template for locating the positioning of individual stakes within the sensor according to the second embodiment.

Turning now to the second embodiment as shown in FIGS. 3 through 5, a seasonal array may be provided in which a plurality of the sensors 16 are installed in an array by insertion into the ground in association with respective plants in a sampling pattern across the region 18. The sampling pattern may follow a conventional serpentine path through the crop field. Only some of the plants are sampled therefore within a given region but at each sampling location a sensor 16 is provided with three stakes 20 which are positioned at a known spacing relative to one another by use of a suitable template 33 which designates the triangular pattern that the stakes are to be placed in relative to one another. Spacing between the stakes thus remains fixed as in the previous embodiment.

The electrodes of all three stakes are commonly connected to a suitable transmitter 34 for transmission of collected data to the processor 30. The transmitter 34 is arranged to only transmit data responsive to a password query by a central processor 30 which is common to many sensors and records data from all of the sensors within a given area. The processor 30 then constructs the representation of electrical impedance across the region. When each sensor 16 is installed, GPS location data along with a unique ID is associated with the sensor at each location so that when the data is transmitted to the central processor 30 a suitable field map can be generated.

In some applications, the first and second embodiments described herein may be combined so that the portable processor may comprise a central processor 30 for the entire system which receives transmitted data from the seasonally installed array while also receiving additional data from sampling at various selected locations by the portable stakes. In this manner the seasonally installed array of sensors may be used to provide an overall perspective of the growth characteristics of a given region, however if there is some indication of a possible problem at one location within the region, additional sampling can be provided by the portable sensors to better assess a potential problem at a given location.

The seasonal array is typically installed after seeding has taken place and before final harvesting. In the meantime, by locating the stakes of each sensor in direct proximity with a respective plant, the stakes of the sensor 16 will not interfere with various crop maintenance activities including cultivating, or spraying and the like. During the early part of the growing season, sampling may be done only once daily or as may otherwise be required for sampling specific problems. During the final bulking stage of the root crop however, it is likely desirable to be increasing the sampling rate up to two or three times per day for example. All of the data collected can then be analysed by a knowledgeable person who can in turn recommend what type of response should be taken depending upon what is indicated by the representation of electrical impedance across the prescribed volume of ground. Additional information including air temperature measurements and the like may be additionally provided to the user to better assess or interpret the representation of electrical impedance generated by the system. The system may be used to compare different areas within a region to improve how the responsiveness of the crop to fertilizer, water and the like is assessed.

The system described herein is particularly useful when combined with existing filed mapping software, for example Ag Management Services provided by John Deere™ and the like. Where GPS maps of fertility variations across a field are already generated within a prescribed region, the crop monitoring system described herein can provide an additional layer of data to the existing field maps for better interpreting the representation of electrical impedance generated by the system. Existing field mapping software can also be used to assist in calibrating the system 10 described herein and in reacting to variations in crop growth with appropriate agronomic practices to increase subsequent crop productivity. Various factors which may assist in obtaining more accurate representations of electrical impedance include determining the soil temperature, the pH level, the soil texture and type including particle size or constitution of minerals, and the base level moisture content of the ground.

The system 10 as described herein has the following functional characteristics and associated benefits:

| Functional Characteristic | Benefits |
| --- | --- |
| RCM senses changes in soil moisture in the root zone of tubers (to a depth of 20 inches) whereas currently available moisture meters are expensive and not very accurate Electrical Impedance Tomography (EIT)—gives an estimated bulk conductivity of a local environment | Accurate moisture sensing information prevents over or under application of water - result will be a reduction in crop stress which reduces sugar ends and other disease issues associated with crop stress. The device will increase crop quality by allowing the grower to reduce crop stresses. Can sense the moisture profile with depth. Many moisture sensors provide readings at the surface. This one can provide moisture estimates at the level of the roots |
| Portable RCM gives non-destructive, three dimensional views of root crops | Allows grower to monitor shape, size and number of developing roots or tubers in real time Grower can then make assessments of when to harvest, and when optimal yields vs. ideal size and shape distribution for processing is reached (optimal harvesting time to maximize financial returns from the crop) Reduces the work of digging 10 foot strips several times to assess the crop—provides a more accurate assessment in less time without destroying crop plants |
| Growth status monitoring over time - crop yield projection with the stationary seasonal stakes EIT can show changes in growth rate before the grower can notice changes in the leaves; therefore the RCM provides an early warning capability of problems that may be mitigated by prompt attention from the grower. | Allows inputs management in real time - grower can act proactively to signals that the crop needs attention—i.e. can top dress with fertilizer, add water, control pests with spot pesticide application Growth curve of tuber bulking can act as an early alert to the grower of stress inducing situations that cause sugar end formation and quality loss in the crop. Plant stress will manifest first as a reduced growth rate in the roots. |
| Yield mapping—development of comprehensive field management plan—GPS capability allows for precision monitoring | Growth rate variance over the field can be monitored and then related to other methods of field status assessments such as soil sampling to determine and optimize crop inputs such as fertilizers, lime (changes pH), soil amendments such as organic matter etc. Yield maps can be utilized over a number of years and various crops to build accurate and precise information tools to help set fertilizer, seeding and crop input rates for various field-specific areas or zones using GPS technology equipped field equipment. |
| RCM collects data on temperature in the rooting zone—EIT is temperature sensitive so the temperature will be part of the calibration system on the device and a parameter that can be monitored | May allow early disease prediction of soil borne diseases—may help grower reduce pesticide requirements |
| Field survey pattern installation of stationary monitoring system will provide data on crop status on a daily basis—real time health monitoring of the crop with little effort from the grower | Allows for early warning of pest infestations (insects or disease) and may reduce necessity to spray entire crop as spot treatments of disease or pests may be adequate to stop spread—could vastly reduce number of pesticide applications - and reduce input costs which will increase profits |
| Remote downloading of data—raw data can go to the grower or to contract agronomists or processors for interpretation | Allows processor's agronomists or service centre support team to closely monitor field status and can assist the processing plant in timing deliveries of specific qualities of crop to maximize consistency on the production line Allows extension specialist to provide zones or provincial maps of growing status, pest infestations and spread over whole districts |
| Ability to sample suspected problem zones non destructively using portable RCM | Portable monitor can be used in fields not equipped with the stationary devices |
| Low cost of production | Hardware is very economical |
| Hardware is very robust | Tool should have few operational or warranty fixes required |

-continued

| Functional Characteristic | Benefits |
| --- | --- |
| Existing field mapping software can be integrated into the system | Reducing cost of manufacture and increasing utility of the device in building yield maps of different crops on the same land |
| System of portable RCM and stationary devices increases the flexibility and utility of the device | Grower can add stationary units as budgets allow but portable unit allows grower to start monitoring for low base price |
| System is modular | Meaning that a grower can start with the lowest cost base kit—the portable monitor and build an inventory of stationary units as their budget allows |
| Data downloading assess codes that are unique and programmable | This allows for information security or sharing depending on operator's wishes - processors and or extension specialists can be given codes |
| Device can be calibrated for various soil types | Part of the software package |
| Device can be calibrated for various root crops | Crops that can be monitored include potato, carrots, peanuts, yams, sweet potato, cassava, sugar beets, agri-forestry, greenhouse plants |
| Existing software packages such as John Deere's Ag Management Solutions packages can easily be integrated into this tool | Creates consistent data collection parameters between crops |
| Sensors may be sensitive enough to use in crop research programs | Determination of how crop conditions affect disease pressures, growth patterns etc., may be used for new variety evaluations in breeding programs etc. Research will be furthered by use of this tool as non destructive sampling technique has never before existed |
| Stationary stakes will not impede wheel traffic and normal field operations can be carried out even when the stakes are present. Stakes are powered by small batteries that turn off and on as only during data recording | Stakes are imbedded beside the plant and will not be affected by hilling or irrigation equipment. Batteries need changing only once per field season. |
| Stationary stakes will only need to be installed once the crop is established - meaning that the grower has already completed most of their field operations and has time to install the stakes at a time when spring seeding is complete | Use of the tool will not interfere with speed of crop establishment or with other field operations |
| Root crop monitor may be sensitive enough to give other information such as soil texture, fertility levels | This information could form part of field assessment parameters collected by technically trained staff to improve cropping methods |
| Integration of GPS technology allows for precision use of other equipment such as sprayers, seeders, fertilizer applicators, irrigation pivots etc. | RCM becomes important data collection device on fields of root crops |
| Number of downloads of data can be programmed by the operator | During times of accelerated growth (late season during tuber bulking) the number of data samples per 24 hour period can be increased |
| Growers and technically trained staff can closely relate field operations to crop status | Irrigation regimes and fertility management with crop status as real-time data gives opportunity to study cause and effect on a growing crop and to make appropriate management decisions to maximize crop potential |

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of monitoring growth characteristics of a plant having a root or root-like structure buried in a prescribed volume of ground, the method comprising:

locating a plurality of electrodes at a known spacing relative to one another in the prescribed volume in proximity to the root or root-like structure;

applying an electrical current to some of the electrodes;

measuring electrical potential at some of the electrodes while the electrical current is applied;

constructing a representation of electrical impedance across the prescribed volume using the measured electrical potential and the known spacing of the electrodes; and identifying a growth characteristic in the prescribed volume by locating variations of electrical impedance in the representation of electrical impedance across the prescribed volume.

2. The method according to claim 1 wherein the variations of electrical impedance comprise a region or volume and wherein the method includes identifying size of a root or root-like structure as defined by the variation of electrical impedance.

3. The method according to claim 1 wherein the variation of electrical impedance comprises a boundary or contour between two regions of differing electrical impedance and wherein the method includes identifying shape of a root or root-like structure as defined by the variation of electrical impedance.

4. The method according to claim 1 including identifying variations of electrical impedance over time intervals to determine variations in moisture content in the ground.

5. The method according to claim 4 including determining a given moisture profile of the ground by comparing the electrical impedance in the representation of electrical impedance across the prescribed volume of ground to a calibrated base level electrical impedance.

6. The method according to claim 1 including inserting the electrodes into the ground spaced below a surface of the ground.

7. The method according to claim 1 including constructing a representation of electrical impedance across the prescribed volume of ground at spaced intervals of time and identifying a growth characteristic by comparing the representation of electrical impedance at different ones of the intervals of time.

8. The method according to claim 1 including measuring temperature in the ground in proximity to the electrodes.

9. The method according to claim 1 including constructing a representation of electrical impedance across the prescribed volume of ground associated with one plant and repeating the construction for a plurality of plants across a given region.

10. The method according to claim 1 including assessing a characteristic of the ground by comparing a constructed representation of electrical impedance of one region with another region.

11. The method according to claim 1 including associating the representation of electrical impedance across the prescribed volume of ground with an existing field map generated by field mapping software.

12. The method according to claim 1 including supporting the electrodes on a portable probe including a portable processor coupled therewith which is arranged to construct the representation of electrical impedance across the prescribed volume of ground.

13. The method according to claim 1 including constructing a representation of electrical impedance for a plurality of plants within a given region by providing a sensor including electrodes thereon associated with each plant.

14. The method according to claim 13 wherein each sensor includes GPS location data and a unique ID associated therewith.

15. The method according to claim 13 wherein each sensor includes data storage means and a transmitter for communicating data to a central processor.

16. The method according to claim 15 wherein the transmitter only transmits data responsive to receipt of a password.

17. The method according to claim 1 including calibrating the electrodes for a prescribed type root or root-like structure by varying the relative positioning and spacing between the electrodes.

18. A crop monitoring system for monitoring a growth characteristic of a plant having a root or root-like structure buried in a prescribed volume of ground, the system comprising;
a plurality of electrodes inserted into the prescribed volume of ground in proximity to the root or root-like structure and at a known spacing relative to one another;
current means arranged to apply a current to at least some of the electrodes;
measuring means arranged to measure an electrical potential of at least some of the electrodes during the current being applied;
processor means arranged to receive the electrical potentials from the measuring means, to construct a representation of electrical impedance across the prescribed volume, and to identify variations of electrical impedance in the representation of electrical impedance across the prescribed volume.

19. The system according to claim 18 wherein the processor means is arranged to identify size or shape of a root-like structure by locating variations of electrical impedance in the representation across the prescribed volume of ground.

20. The system according to claim 18 wherein the processor means is arranged to identify an overall electrical impedance profile of the ground and determine a difference between the overall electrical impedance profile and a calibrated base level impedance profile to determine a moisture pattern of the soil in the ground.

* * * * *